United States Patent
Faure

(10) Patent No.: US 10,517,918 B2
(45) Date of Patent: Dec. 31, 2019

(54) USE OF A MODIFIED SWEET WHEY AND A MODIFIED SWEET WHEY CONTAINING INFANT FORMULA FOR PROMOTING THE POSTNATAL DEVELOPMENT OF THE INFANT CENTRAL NERVOUS SYSTEM AND RELATED COGNITIVE FUNCTIONS

(71) Applicant: NESTEC S.A., Vevey (CH)

(72) Inventor: Magali Faure, Forel (CH)

(73) Assignee: Societe des Produits Nestle S.A., Vevey (CH)

( * ) Notice: Subject to any disclaimer, the term of this patent is extended or adjusted under 35 U.S.C. 154(b) by 282 days.

(21) Appl. No.: 15/103,521

(22) PCT Filed: Dec. 12, 2014

(86) PCT No.: PCT/EP2014/077484
§ 371 (c)(1),
(2) Date: Jun. 10, 2016

(87) PCT Pub. No.: WO2015/086789
PCT Pub. Date: Jun. 18, 2015

(65) Prior Publication Data
US 2016/0310557 A1    Oct. 27, 2016

(30) Foreign Application Priority Data

Dec. 13, 2013 (EP) .................................. 13197205

(51) Int. Cl.
| | |
|---|---|
| A61K 38/40 | (2006.01) |
| A61K 38/01 | (2006.01) |
| A61K 35/20 | (2006.01) |
| A23L 33/00 | (2016.01) |
| A23L 33/19 | (2016.01) |
| A61K 35/745 | (2015.01) |
| A61K 35/747 | (2015.01) |
| A61K 9/00 | (2006.01) |
| A61K 35/741 | (2015.01) |

(52) U.S. Cl.
CPC ............ *A61K 38/018* (2013.01); *A23L 33/19* (2016.08); *A23L 33/40* (2016.08); *A61K 9/0053* (2013.01); *A61K 35/20* (2013.01); *A61K 35/741* (2013.01); *A61K 35/745* (2013.01); *A61K 35/747* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2008/0003330 | A1 | 1/2008 | Rueda et al. |
| 2012/0148679 | A1 | 6/2012 | Mathisen et al. |
| 2012/0184483 | A1* | 7/2012 | Faure ............... A61K 38/40 514/2.5 |
| 2012/0184484 | A1* | 7/2012 | Wang ............... A61K 38/40 514/2.5 |
| 2015/0250222 | A1 | 9/2015 | Secretin |

FOREIGN PATENT DOCUMENTS

| | | |
|---|---|---|
| CN | 1358067 A | 7/2002 |
| CN | 101773223 | 7/2010 |
| EP | 0880902 | 12/1998 |
| EP | 2251030 | 11/2010 |
| RU | 2346448 C2 | 2/2009 |
| WO | 0141580 | 6/2001 |
| WO | 2008108651 | 9/2008 |
| WO | 2013138157 | 9/2013 |

OTHER PUBLICATIONS

Website document entitled: "Sweet whey powder" (available at http://www.thinkusadairy.org/products/whey-protein-and-ingredients/whey-categories/sweet-whey-powder). Downloaded from website Sep. 14, 2018 (Year: 2018).*
Ulber et al. (2001) Acta Biotechnol. 21: 1, 27-34. (Year: 2001).*
Mortensen et al., "Effects of different fractions of whey protein on postprandial lipid and hormone responses in type 2 diabetes", European Journal of Clinical Nutrition, May 16, 2012, vol. 66, pp. 799-805.
Pizova N.V. Cognitive disorders in infants, Consilium Medicum, Annex Pediatry 2011 N4 [On-line] (retrieved on Jun. 26, 2018] (http://con-med.ru/magazinas/pediatry-04-2011).
Russia Patent Office Communication for corresponding Application No. 2016128274/04(044167), dated Oct. 31, 2018, 10 pages.

* cited by examiner

*Primary Examiner* — Russell G Fiebig
(74) *Attorney, Agent, or Firm* — K&L Gates LLP

(57) ABSTRACT

The invention relates to modified sweet whey protein (MSWP) for promoting the establishment of healthy and normal cognitive function in young mammals. In particular, the invention relates to the use of MSWP for promoting development of the brain structures responsible for cognitive functions (e.g. cortex and its associated neural pathways) and/or to reverse retardation and/or to prevent retardation of the establishment of cognitive functions. Humans or animals and, in particular, a foetus, pre-term or term born infant, toddler or child or a young adult may benefit from the invention.

18 Claims, 1 Drawing Sheet

USE OF A MODIFIED SWEET WHEY AND A MODIFIED SWEET WHEY CONTAINING INFANT FORMULA FOR PROMOTING THE POSTNATAL DEVELOPMENT OF THE INFANT CENTRAL NERVOUS SYSTEM AND RELATED COGNITIVE FUNCTIONS

CROSS REFERENCE TO RELATED APPLICATIONS

The present application is a National Stage of International Application No. PCT/EP2014/077484, filed on Dec. 12, 2014, which claims priority to European Patent Application No. 13197205.1, filed Dec. 13, 2013, the entire contents of which are being incorporated herein by reference.

FIELD OF THE INVENTION

The present invention relates generally to the field of neuronal health, neuronal protection and neuronal development. The invention specifically relates to administration of sweet whey protein capable of promoting the healthy establishment of cognitive function in infants, especially preterm, small for gestational age, low birth, very low and extremely low birth weight infants.

BACKGROUND TO THE INVENTION

The central nervous system (CNS), and in particular the brain, drives the cognitive functions. The cerebral cortex, which is a sheet of neural tissue that is outermost to the cerebrum of the mammalian brain, plays a key role in attention, perceptual awareness, thought, language, higher order cognition (executive function) and information integration of sensory input.

Central nervous system development and maturation is a highly complex biological phenomenon that involves a number of physiological processes including, for example, neuron and glial cell growth and differentiation, neuronal pathfinding and branching, and establishment of inter neuronal communication (nerve signals) via axon growth and neurotransmitter release. Furthermore, although not all axons are myelinated, myelination (an important function of glial cells) is necessary to insulate the electrical signal carried along the axons, thereby ensuring efficient signal transmission, and preventing cross talk between neighbouring nerves. [Baumann, N. and Pham-Dinh, D. (2001); Biology of Oligodendrocyte and Myelin in the Mammalian Central Nervous System, *Physiological Reviews,* 81(2): 871-927]; [Deoni, S. C. et al. (2011); Mapping infant brain myelination with magnetic resonance imaging, *J. Neurosci.,* 31(2): 784-91]. Myelination is partially regulated by Myelin Basic Protein.

Myelination begins during pregnancy and continues up until and during adolescence/early adulthood (until 20 years old) [Baumann, N. and Pham-Dinh, D. (2001)]; [Benton, D. (2010); Neurodevelopment and neurodegeneration: are there critical stages for nutritional intervention?, *Nutr. Rev.,* 68 Suppl. 1: S6-10]. Myelination is one of the last brain developmental processes to take place and is one of the first to decline in aging. Thus, optimal myelination achieved early in life may limit its early decline.

Disrupted myelination during neuronal/brain development may contribute or worsen disorders such as autism, attention deficit/hyperactivity disorder and schizophrenia. Moreover, disorders associated with destruction of myelin insulation include multiple sclerosis, and, later in life, Alzheimer's disease.

Neuronal plasticity, which is defined as the ability of the brain to continuously adapt its functionally and structural organization to changing requirements is important in nervous system maturation. It is essential for the correct functioning of the brain and necessary for cognition, learning and memory. Some of the neuronal markers, including proteins and neurotrophic factors, like Brain Derived Neurotrophic Factor (BDNF) required for, or at least, associated with these physiological processes, have been identified in the literature and studied [Huang, E. J. and Reichardt, L. F. (2001); Neurotrophins: Roles in Neuronal Development and Function, *Annu. Rev. Neurosci.,* 24: 677-736]; [Musumeci, G. and Minichiello, L. (2011); BDNF-TrkB signalling in fear learning: from genetics to neural networks, *Rev. Neurosci.,* 22(3): 303-15]; [Xiao, J. et al. (2009); The role of neurotrophins in the regulation of myelin development, Neurosignals, 17: 265-276] and [Von Bohlen and Halbach, 0. (2011); Immunohistological markers for proliferative events, gliogenesis, and neurogenesis within the adult hippocampus, Cell Tissue Res., 345(1):1-19].

The central nervous system develops during gestation and then refines to a mature, functional network during the post natal period. In humans foetuses, the cerebral cortex develops quite late and over a protracted period of time.

In utero, there is a strong acceleration of neuronal/brain maturation and growth from week 30 of gestation in humans.

Premature babies show very basic electrical activity in the primary sensory regions of the cerebral cortex—those areas that perceive touch, vision, and hearing, as well as in primary motor regions of the cerebral cortex. These babies enter the world with a still-primitive cerebral cortex, and it is the gradual maturation of this complex part of the brain that explains much of their emotional, social and cognitive maturation in the first few years of life [Lubsen, J. et al. (2011); Microstructural and functional connectivity in the developing preterm brain, Seminars in Perinatology, 35, 34-43].

Preterm babies are born at a time that is crucial for structural and functional brain development and maturation and, so, they miss out on in utero brain development. They are at risk for medical conditions after birth, including hemorrhagic and hypoxic-ischemic brain injuries, as well as for development problems later in life, including cognitive deficits. This risk seems to be higher the younger the babies are delivered and the lower their birth weight is. Cognitive deficits in terms of lower IQ, lower attention and working memory abilities, and problems in executive functions may persist into school-age and adolescence [Talge, N. et al. (2010). Late-Preterm Birth and its Association with Cognitive and Socioemotional Outcomes at 6 Years of Age. Pediatrics, 126, 1124-1131; van Baar, A., et al. (2009). Functioning at school age of moderately preterm children born at 32 to 36 weeks' gestational age. Pediatrics, 124, 251-257; Farooqi, A et al. (2011). Impact at age 11 years of major neonatal morbidities in children born extremely preterm. Pediatrics, 127, e1247-1257; Nosarti, C. et al. (2010). Neurodevelopmental outcomes of preterm birth. Cambridge: Cambridge University Press].

Non-severe cases (low prematurity, for example, birth at 32 to <37 weeks; WHO, 2013, http://www.who.int/mediacentre/factsheets/fs363/en/) will likely "catch-up" their suboptimal neuronal/brain maturation ex utero. However, because this maturation occurs in the presence of external stimuli (sounds, light, smell etc.) different from the in utero environment and the occurrence of brain damage due to prematurity, this "catch-up" brain maturation may be impacted, compared to that occurring in utero. The infant may experience difficulties in processing external information at the premature stage. This early setback in brain development carries the risk of sub-optimal cognitive abilities during the infant's subsequent development.

For the reasons outlined above, in severely premature infants (including extremely preterm infants, born at less than 28 weeks, and very preterm infants born between 28 and 32 weeks) the incidence of sub-normal cognitive function is more marked.

More generally CNS immaturity or delayed maturation of the CNS, can be observed in infants such as:
Preterm infants, low birth weight (<2500 g), very low and extremely low birth weight infants (<1500 g), extremely low birth weight (<1000 g) and in small for gestational age infants [Allen, M. C. (2008); Neurodevelopmental outcomes of preterm infants, *Curr. Opin Neurol.*, 21(2): 123-8].
Premature or term-born infants having experienced an intrauterine growth retardation (IUGR) that occurred following any adverse events during the gestation (smoking of the mother, medication of the mother, low placenta quality, abnormal placenta positioning, malnutrition of the mother and the foetus, excessive stress/anxiety of the mother, etc); [Gregory, A. et al. (2008); Intrauterine Growth Restriction Affects the Preterm Infant's Hippocampus, *Pediatric Research*, 63(4): 438-443].
Any neonate and young infant showing nervous system growth retardation following, for example, hypoxemia-ischemia at birth, postnatal complications, postnatal steroid treatments or any other adverse event [Barrett, R. D. et al. (2007); Destruction and reconstruction: hypoxia and the developing brain, *Birth Defects Res. C. Embryo Today*, 81: 163-76].

Cognitive dysfunctions are reported in these infants, along with dysfunction in their growth and development, indicating that an optimal "catch-up" of the neurodevelopmental process is not achieved.

Immaturity or delayed maturation of the cerebral cortex can lead to delayed and/or impaired learning ability, information integration, processing of sensory input, loss of, or poor development of higher reasoning, executive functions, concentration, attention, motor skills and language. This may lead to behavioral problems abnormally low intelligence, and thus, abnormally low mental performance.

Behavioral and neurodevelopmental disorders associated with delayed maturation of the cerebral cortex include attention deficit/hyperactivity disorders and autism spectrum disorders.

Thus, if the foetus, neonate or infant has experienced central nervous system growth retardation, it is desirable that this retardation be reversed quickly, and that any further retardation be prevented, so that the central nervous system development "catches up" to a normal level and that the growing foetus or infant experiences minimal cognitive function impairment later in life.

Cognitive function may be measured in humans with clinical tests, that depend on age; many such tests known to pediatricians and child development experts. For babies and infants, development screening and neurodevelopment tests exist such as for example, BSID—Bayley Scales of Infant Development, Brazelton Neonatal Behavioral Assessment Scale, NEPSY—A Developmental NEuroPSYchological Assessment and Griffiths Mental Development Scales. For pre-school and/or school children tests for cognitive abilities include PPVT (Peabody Picture Vocabulary Test), TONI-2 (Test of Nonverbal Intelligence-2), WPPSI (Wechsler Pre-school and Primary Scales of Intelligence), and CPM (Raven's Coloured Progressive Matrices).

It is known that nutrition plays an important role in neuronal maturation in the brain (reviewed in [Huppi, P. S. (2008); Nutrition for the Brain, *Pediatric Research,* 63(3): 229-231]). Specifically, clinical studies have shown that essential fatty acids, are crucial to ensure foetal and post-natal brain development [Chang, C. Y. et al. (2009); Essential fatty acids and human brain, *Acta Neurol. Taiwan,* 18(4): 231-41]; [Alessandri, J. M. et al. (2004); Polyunsaturated fatty acids in the central nervous system: evolution of concepts and nutritional implications throughout life, *Reprod. Nutr. Dev.,* 44(6): 509-38].

The consequences of malnutrition can be irreversible and may include poor cognitive development, educability, and thus future economic productivity. [Horton, R; (2008) The Lancet, Vol. 371, Issue 9608, page 179; [Laus, M. F. et al. (2011); Early postnatal protein-calorie malnutrition and cognition: a review of human and animal studies, *Int. J. Environ. Res. Public Health.,* 8(2): 590-612].

It is known that both parental nutrition as well as breast milk of mothers after premature birth provide insufficient nutritional support to the developing brain. Thus, oral interventions are an appropriate way to positively impact on the development of the nervous system, so as to ensure normal development of cognitive function and mental performance in the preterm or term born neonate, infant, toddler, child or young adult or young animal.

There is a need to promote and support the healthy establishment of cognitive function, and/or to reverse retardation and/or to prevent further delay of the establishment of cognitive function at the earliest possible stage during gestation, as well as during the early phases of newborn life, when the nervous system is rapidly maturing.

Because the central nervous system and, in particular, parts of the cortex and the hippocampus, develop until adolescence/early adulthood (20 years), there is a need to provide nutritional support for the healthy establishment and development of cognitive function throughout the young life of the child until adolescence. In particular, there is a need to prevent or treat the severity of disorders such as impaired learning ability, loss of, or poor development of higher reasoning, abnormally low concentration, including Attention Deficit Hyperactivity Disorder (ADHD), delay in language development, memory and executive function problems, abnormally low intelligence, and thus, abnormally low mental performance in children from birth to early adulthood (20 years old).

There is a need to provide a treatment of these disorders in patients who have been diagnosed with cognitive function impairment. There is a need to provide a prophylactic treatment for young mammals in the population groups defined above who are at risk of cognitive function impairment. There is a need to provide a composition to be used in such treatments.

There is a need to positively impact neuronal maturation in the brain of young mammals, in particular, the structures of the brain associated with cognitive function. Specifically, there is a need to positively impact neuronal growth, survival, plasticity and differentiation. There is a need to positively impact signal transmission in the brain by supporting myelination.

There is a need to provide such treatment, prophylactic treatment or such related composition in a form that is well accepted by the subject population, in particular those of in these populations that are the most fragile or the most in need. There is a further need to not induce disadvantages, side-effects or negatives in such population. There is a need to provide such solutions to the subject populations in the most simple and most cost-effective way.

The present invention applies to all mammals, including animals and humans.

SUMMARY OF THE INVENTION

The invention relates to modified sweet whey protein (MSWP) for promoting the establishment of healthy and normal cognitive function in young mammals. The modified sweet whey protein of the invention comprises 30%-100% w/w protein, preferably >80% w/w protein. Thus, the MSWP may be in the form of a sweet whey protein isolate or a sweet whey protein concentrate. The MSWP is a SWP from which caseino-glyco-macropeptide (CGMP) has been substantially removed. The MSWP may be partially or extensively hydrolyzed.

The MSWP according to the invention may be used for promoting the healthy establishment of cognitive function and/or prevention of, or repair of, or reduction in the severity of cognitive function impairment in a young mammal.

It may further be used for treatment of disorders associated with the delayed establishment of cognitive function or cognitive function impairment in a young mammal.

The disorders may be any one or more of the following: delayed and/or impaired learning ability, loss of, or poor development of executive functions, higher reasoning impairment, memory impairment, delay in language development, learning disabilities, abnormally poor concentration including Attention Deficit Hyperactivity Disorder (ADHD), abnormally decreased intelligence, abnormally poor mental performance, mood disturbance, or autism.

Humans or animals and, in particular, a foetus, pre-term or term born infant, toddler or child or a young adult up to the age of twenty years old may benefit from the invention.

The invention may be especially beneficial to those infants having experienced IUGR, or having a low, very low or extremely low birth weight, being small for gestational age, having suffered hypoxemia-ischemia at birth, postnatal complications, postnatal steroid treatments or any other adverse event in the post natal period, and/or suffering from cognitive function impairment, such as impaired learning and memory, lack of curiosity, poor attention span and thus, poor mental performance, central nervous system growth retardation, either in utero, or, during or after birth.

The present inventors have found that administration of MSWP promotes neuronal and glial development in young mammals. It ensures healthy neuronal growth, survival, differentiation and plasticity, as well as promoting axon myelination. Administration of MSWP may increase expression levels of Brain Derived Neurotrophic Factor (BDNF), and Myelin Basic protein (MBP) in the cortex of the young mammal.

The administration of the sweet whey protein may be to a foetus via the mother. It may also be to a pre-term or term-born infant either directly or via mothers' milk. The administration may be also be to a child or young adult, generally up to the age of twenty years old, or the equivalent age in an animal.

The MSWP may be administered directly to the infant or young child in its pure form, or diluted in water or breast milk, in a food supplement, or together with in a milk fortifier, or any milk support used during trophic feeding, in an infant formula, or in a milk based drink. The modified sweet whey protein is administered to the infant, or young child as a daily dose of 30 to 80%, preferably 60% w/w, of the total protein intake.

The administration period for the foetus is generally at least one week, preferably two weeks, more preferably at least one month, and the administration period for the infant or young child is generally at least 4 weeks, preferably 2-12 months, and more preferably at least 18 months and even more preferably up until the child is in the early adulthood (20 years old).

The MSWP may be administered to pre-term or term-born infant, or child or young adult as a dose of 1.6-3.2 g protein/100 kca, preferably, 1.6-2.2 g protein/100 kca, and more preferably 1.8-2.1 g protein/100 kcal. In one embodiment the MSWP is administered to the infant as a dose of 1.0 to less than 1.6 g protein/100 kca.

The invention relates to a composition comprising 30-80%, preferably 60% sweet whey protein, for healthy establishment and development of cognitive function throughout the young life of the child until adolescence or even until age twenty. In particular, it relates to a composition for the prevention/reduction of the severity of disorders such as impaired learning ability, loss of, or abnormally poor higher reasoning, abnormally poor concentration including ADHD, delay in language development, memory and executive function problems, abnormally low intelligence, and thus, abnormally low mental performance and autism in a young mammal.

The invention may be particularly useful for those young mammals who are born prematurely or who have suffered from IUGR.

DETAILED DESCRIPTION

Definitions

Figure 1:
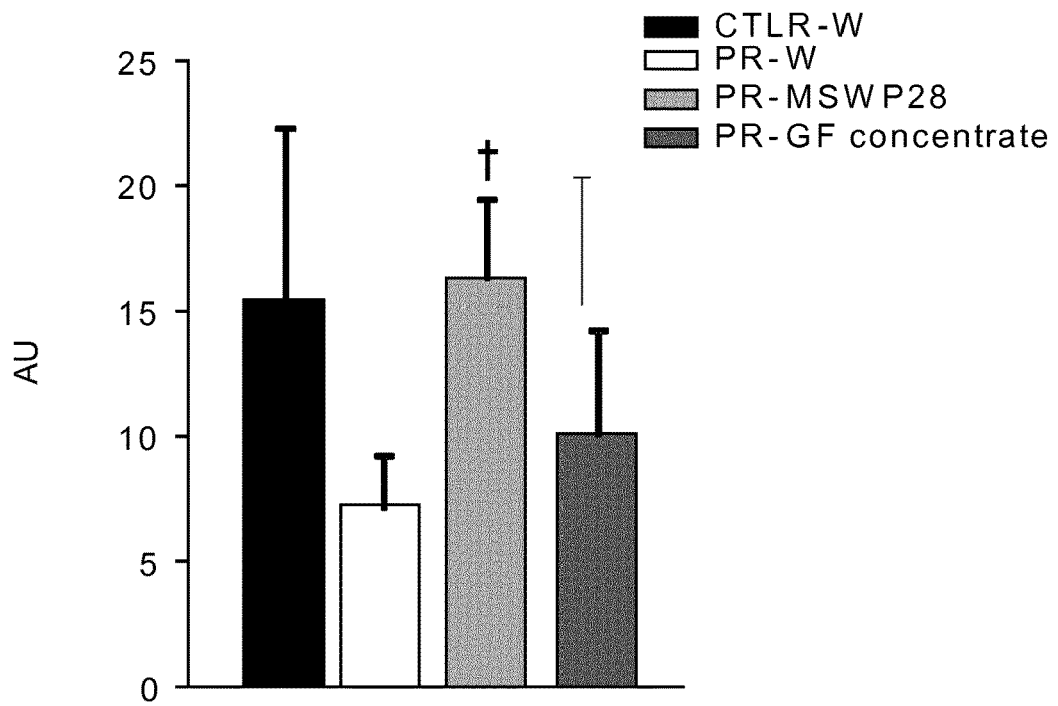
FIG. 1 Mature Brain Derived Neurotrophic Factor BDNF protein levels in the cortex of CTRL-W, PR-W and PR pups supplemented with different milk fractions. Results are expressed in arbitrary units and are medians±SEMedian, n=6, P<0.05; * vs. CTRL-W and † vs. PR-W. Abbreviations are PR: protein restriction; W: water; MSWP28: modified sweet whey P28; GF: Growth factor.

In this specification, the following terms have the following meanings:

"Infants": according to the Commission Directive 2006/141/EC of 22 Dec. 2006 on infant formulae and follow-on formulae, article 1.2 (a), the term "infants" means children under the age of 12 months.

"Post natal period" is the period beginning immediately after the birth of a child and extending for about six weeks "Neonate" generally means an infant up until the age of 6 months.

"Pre-term infant" generally means an infant born before 37 weeks gestation.

"Term born infant" generally means an infant born after 37 weeks gestation.

"Young mammal" generally means a mammal up to the age of twenty years old for a human and the equivalent age in animals.

"Child" generally means a human up to the age of eighteen.

"Toddler" generally means a child from when he can walk up to three years old.

"Modified Sweet Whey Protein" (MSWP) or "Modified Sweet Whey" (MSW) means sweet whey protein from which some or all of the caseino-glyco-macropeptide (CGMP) has been removed. In various embodiments of the invention the MSW is depleted by more than 60%, more than 75%, more than 90%, more than 95% or more than 99% (w/w) of its caseino-glyco-macropeptide (CGMP) in comparison to the amount present in average in native sweet whey of the same origin (for example bovine sweet whey).

"Cognitive Function" refers to an intellectual process by which one becomes aware of, perceives, or comprehends ideas. It involves all aspects of perception, attention, thinking, reasoning, understanding and remembering.

"Higher reasoning" refers to the process of thinking about something in a logical way in order to form a conclusion or judgment. It can also be referred to as executive functions.

"Treat" or "treating" means any treatment, including, but not limited to, alleviating symptoms, eliminating the causation of the symptoms either on a temporary or permanent basis, or preventing or slowing the appearance of symptoms and progression of the named disorder or condition.

"Probiotic" means microbial cell preparations or components of microbial cells with a beneficial effect on the health or well-being of the host. [Salminen, S. et al. (1999); Probiotics: how should they be defined, *Trends Food Sci. Technol.*, 10 107-10]. The definition of probiotic is generally admitted and in line with the WHO definition. The probiotic can comprise a unique strain of micro-organism, a mix of various strains and/or a mix of various bacterial species and genera. In case of mixtures, the singular term "probiotic" can still be used to designate the probiotic mixture or preparation. For the purpose of the present invention, microorganisms of the genus *Lactobacillus* are considered as probiotics.

"Prebiotic" generally means a non-digestible food ingredient that beneficially affects the host by selectively stimulating the growth and/or activity of micro-organisms present in the gut of the host, and thus attempts to improve host health.

"Allergy" means an allergy which has been detected by a medical doctor and which can be treated occasionally or in a more durable manner. A "food allergy" is an allergy with respect to a nutritional composition.

"Infant formulae": according to the Commission Directives 2006/141/EC of 22 Dec. 2006 and/or 91/321/EEC of 14 May 1991 on infant formulae and follow-on formulae, article 1.2 (c), the term "infant formulae" means foodstuffs intended for particular nutritional use by infants during the first four to six months of life and satisfying by themselves the nutritional requirements of this category of persons. It has to be understood that infants can be fed solely with infant formulas, or that the infant formula can be used by the carer as a complement of human milk. It is synonymous to the widely used expression "starter formula".

"Follow-on formulae": according to the Commission Directives 2006/141/EC of 22 Dec. 2006 and/or 91/321/EEC of 14 May 1991 on infant formulae and follow-on formulae, article 1.2 (d), the term "follow-on formulae" means foodstuffs intended for particular nutritional use by infants aged over four months and constituting the principal liquid element in a progressively diversified diet of this category of persons.

"Growing-up milk": milk-based nutritional composition especially adapted to a child of between one year and three years old.

"Human Milk fortifier": Nutritional composition for infants or young children intended to be added to or diluted with human milk.

The term "hypoallergenic composition" means a composition which is unlikely to cause allergic reactions.

The term "sialylated oligosaccharide" means an oligosaccharide having a sialic acid residue.

The term "fucosylated oligosaccharide" means an oligosaccharide having a fucose residue.

All percentages are by weight unless otherwise stated.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

Dietary protein provides the essential amino acids necessary for protein synthesis and growth and protein quality is as important as protein quantity. The present invention provides sweet whey protein, for use by administration for the promotion of the healthy establishment of effective cognitive function and specifically the treatment of the following disorders: impaired learning ability, loss of, or poor development of higher reasoning, concentration difficulties, delay in language development, memory and executive function problems, abnormally low intelligence, and thus, abnormally low mental performance, autism in a young mammal.

The protein fraction in cows' milk is a mixture of several proteins, all of which have a different amino acid profile. Caseino-glyco-macropeptide (CGMP) is derived from the proteolysis of kappa-casein to give para-kappa-casein, an insoluble fraction that remains in the casein fraction, and CGMP, a soluble fraction that is found in the whey fraction. The sweet whey protein of the invention is a modified sweet whey fraction, that is, a sweet whey protein which has a reduced level of caseino-glyco-macropeptide (CGMP) compared to classical sweet whey protein. This sweet whey fraction is termed modified sweet whey (MSW). A classical sweet whey can contain from 4 to 40% of CGMP according to the milk processing. The starting sweet whey may be obtained from cheese making, particularly the sweet whey obtained after the coagulation of casein by rennet.

The reduced CGMP whey fraction or MSW according to the invention provides the advantage of a reduced threonine content and an increased tryptophan content as compared to normal (unmodified) sweet whey and is therefore suitable as a protein source for infants.

This modified sweet whey fraction may be further treated to remove minerals (cations, anions), lactose, or any of these substances. The sweet whey may be concentrated as desired. Suitable sweet whey sources are commercially available.

The removal of caseino-glyco-macropeptide may be accomplished by any suitable process. One suitable process is described in EP0880902. In this process, the pH of the sweet whey is adjusted to 1 to 4.3, if necessary. The sweet whey is then contacted with a weakly anionic resin which is predominantly alkaline until the pH of the sweet whey stabilizes at about 4.5 to 5.5. The sweet whey fraction from which the required quantity of the caseino-glyco-macropeptide has been removed, is then collected. According to one embodiment of the invention this reduced CGMP whey protein fraction contains approximately 28% protein, of which CGMP accounts for, 2 to 3% of total protein, and is thus termed "MSWP28".

The MSW for use according to the invention may, of course, contain a higher percentage of protein than in MSWP28, for example from 30 to 99%, protein.

The MSWP may be non-hydrolysed. Alternatively, the modified sweet whey protein fraction may be partially or extensively hydrolysed to prevent allergic reactions in infants at risk of allergy and to make the protein easier to digest. The hydrolysis process may be carried out as desired and as is known in the art. In general, the whey protein hydrolysate is prepared by enzymatically hydrolysing the sweet whey fraction in one or more steps. For example, for an extensively hydrolysed protein, the sweet whey proteins may be subjected to triple hydrolysis using, for example, Alcalase 2.4L (EC 940459), then Neutrase 0.5L (available from Novo Nordisk Ferment AG) and then pancreatin at 55° C. Alternatively, for a protein fraction that is hydrolysed to a lesser degree, the sweet whey may be subjected to double hydrolysis using, for example, NOVOZYMES and then pancreatin.

If the MSWP used is substantially lactose free, it is found that the protein is subjected to much less lysine blockage during the hydrolysis process. This enables the extent of lysine blockage to be reduced from about 15% by weight of total lysine to less than about 10% by weight of lysine; for example about 7% by weight of lysine. This greatly improves the nutritional quality of the protein source.

Doses of MSWP

The modified sweet whey protein may be administered to infant, or young child as a dose of 1.6-3.2 g protein/100 kca, preferably 1.6-2.2 g protein/100 kca, and even more preferably 1.8-2.1 g protein/100 kcal.

For preterm born babies there are specific recommendations, published by the ESPGHAN Committee on Nutrition, on the amount of protein that they should receive. For the case for preterm babies born weighing less than 1 kg, the recommended protein content intake is 3.6 to 4.1 g protein/100 kcal. For infants born with a birthweight of between 1 to 1.8 kg, the recommended protein content intake is 3.2 to 3.6 g protein/100 kcal [Agostini et al (2010) JPGN 2010 (50), 1, Enteral Nutrient Supply for Preterm Infants].

Thus, the amount of MSWP administered to the pre-term infant is appropriately adapted according to the current recommendations. For example, if according to one embodiment of the invention the SWP has a protein content of 100%, and the MSWP represents 80% of the total protein being administered to the preterm infant, then a suitable quantity of SWP to be administered to the preterm infant is 2.8-3.2 g per 100 kcal for infants of less than 1 kg and 2.5-2.9 for infants of 1 kg-1.8 kg body weight.

The dose of MSWP administered is such that the protein intake of the subject is within the appropriate guidelines (for example, WHO or ESPGHAN committee recommendations).

For example, in a preferred embodiment a composition comprises about 9.0 to about 10.0 w/w % of protein, more preferably about 9.5% w/w %. This corresponds to about 1.8 g protein/100 kcal. An advantage provided by this concentration of protein is that it is equivalent to the amount of protein generally present in human milk and it corresponds to the lower limit described in the *Codex Alimentarius*.

Generally, the MSWP may represent between about 70 to about 100% of the total protein in the composition. Thus, it may also represent 75%, 80%, 85%, 90%, or 95% of the protein in the composition.

Thus, the modified sweet whey protein of the invention may be generally administered to an infant or young child as a dose of 1.6-3.2 g protein/100 kca, preferably 1.6-2.2 g protein/100 kca and even more preferably 1.8-2.1 g protein/100 kcal.

Method of Administration (i) Administration to Infants

The MSWP may be administered orally directly to the infants alone (pure or diluted in water or mother's milk for example) as a food supplement (for example, as, or together with a human milk fortifier supplement), or any milk support used during trophic feeding, or as a pharmaceutical or nutriceutical composition, or as an ingredient in an infant milk formula. Such a formula may be an infant "preterm formula" if the progeny is born before term or has a low birth weight, a "starter formula" or a "follow-on formula". The formula may also be an hypoallergenic (HA) formula in which the cow milk proteins are hydrolysed. An example of such starter formula is given in Example 2. The MSWP may be administered as a growing-up milk or in any milk-based drink.

(ii) Administration to Children

The MSWP may also be administered orally to children in the form of a pharmaceutical or nutraceutical composition, growing-up milk, milk based drinks, food supplements, milk based yoghurts, desserts and puddings, biscuits and cereal bars, cereals and fruit-based drinks.

(iii) Administration to Expectant or Lactating Mothers

The MSWP may also be administered to expectant or lactating mothers orally, preferably in foods, drinks, dietary supplements or pharmaceutical compositions.

(iv) Administration to Animals

The SWP may also be administered orally to animals alone, or in water or in the form of a food supplement, a pharmaceutical or nutriceutical composition, or milk or pet food.

Administration with Other Compounds

The MSWP can be administered alone (pure, or diluted in water or milk, including breast milk for example) or in a mixture with other compounds (such as dietary supplements, nutritional supplements, medicines, carriers, flavours, digestible or non-digestible ingredients). Vitamins and minerals are examples of typical dietary supplements. In a preferred embodiment, MSWP is administered in a composition, for example, an infant formula, together with other compounds that enhance the described beneficial effect on the young mammals. For example this may be a probiotic.

Other probiotics may be administered also. Preferably, the probiotic may be selected for this purpose from the group consisting of *Bifidobacterium, Lactobacillus, Lactococcus, Enterococcus, Streptococcus, Kluyveromyces, Saccharoymces, Candida*, in particular selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus lactis, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii* or mixtures thereof, preferably selected from the group consisting of *Bifidobacterium longum* NCC3001 (ATCC BAA-999), *Bifidobacterium longum* NCC2705 (CNCM I-2618), *Bifidobacterium longum* NCC490 (CNCM I-2170), *Bifidobacterium lactis* NCC2818 (CNCM I-3446), *Bifidobacterium breve* strain A, *Lactobacillus paracasei* NCC2461 (CNCM I-2116), *Lactobacillus johnsonii* NCC533 (CNCM I-1225), *Lactobacillus rhamnosus* GG (ATCC53103), *Lactobacillus rhamnosus* NCC4007 (CGMCC 1.3724), *Enterococcus faecium* SF 68 (NCC2768; NCIMB10415), and mixtures thereof.

Other examples of synergistic compounds that may be included in the compositions, especially infant formula, of the invention are prebiotic compounds. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon, where they are selectively fermented by the beneficial bacteria. Examples of prebiotics include certain oligosaccharides, such as fructooligosaccharides (FOS), cow milk oligosaccharides (CMOS), and galactooligosaccharides (GOS). A combination of prebiotics may be used such as 90% GOS with 10% short chain fructo-oligosaccharides such as the product sold under the trade mark Raftilose® or 10% inulin such as the product sold under the trade mark Raftiline®. Other examples of prebiotics that can be used in the context of the present invention include the group of oligosaccharides obtained from milk or other sources, optionally containing sialic acid, fructose, fucose, galactose or mannose. Preferred prebiotics are sialo-oligosaccharides (SOS), fructo-oligosaccharides (FOS), galacto-oligosaccharides (GOS), isomalto-oligosaccharides (IMO), xylo-oligosaccharides (XOS), arabino-xylo oligosaccharides (AXOS), mannan oligosaccharides (MOS), oligosaccharides of soy, glycosylsucrose (GS), lactosucrose (LS), sialyl-lactose (SL), fucosyl-lactose (FL), Lacto-N-Neotetraose (LNNT), lactulose (LA), palatinose-oligosaccharides (PAO), malto-oligosaccharides, gums and/or hydrolysates thereof, pectins, starches, and/or hydrolysates thereof. An infant formula according to the invention preferably further contains at least one prebiotic in an amount of 0.3 to 10% of the total weight of the dry composition.

In particular, the human milk oligosaccharides, for example sialylated oligosaccharides, described in WO 2012/069416 published on May 31, 2012 may be included in the composition according to the invention. The latter oligosaccharides may act in synergy with the MSWP of the invention to promote the healthy development of the mammalian central nervous system in the infant or child.

The daily doses of carbohydrates, and all other compounds administered with the MSWP should always comply with the published safety guidelines and regulatory requirements. This is particularly important with respect to the administration to new-born babies, especially those born with low birth weight, very low or extremely low birth weight.

A composition, for example infant formula, containing the MSWP for administration according to one embodiment of the invention may contain a further protein source in an amount so that the total protein is not more than 4.0, 3.0 or 2.0 g/100 kcal, preferably 1.8 to 2.0 g/100 kcal. It is preferred that over 50% by weight of the protein source is modified sweet whey (MSW). The type of additional protein source is not believed to be critical to the present invention provided that the minimum requirements for essential amino acid content are met and satisfactory growth is ensured although. In one embodiment, the protein content is between 30% and 80% modified whey proteins. Thus, additional protein sources such as unmodified sweet whey protein, skimmed milk, casein or soy may be used. In one embodiment the casein/whey ratio is between 70/30 and 20/80.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art.

The composition may also comprise a source of carbohydrates and/or a source of fat. The infant formula may contain a source of lipids. The lipid source may be any lipid or fat which is suitable for use in infant formulas. Preferred fat sources include palm oil, high oleic sunflower oil and high oleic safflower oil. The essential fatty acids, linoleic and α-linolenic acid may also be added. One or more essential long chain fatty acids (LC-PUFAs) may be included in the composition. Examples of LC-PUFAs that may be added are docosahexaenoic acid (DHA) and arachidonic acid (AA). The LC-PUFAs may be added at concentrations so that they constitute greater than 0.01% of the fatty acids present in the composition. They may be added as small amounts of oils containing high quantities of pre-formed arachidonic acid and docosahexaenoic acid such as fish oils or microbial oils. Palmitic acid may be added, preferably in the Sn-2 position. In total, the fat content is preferably such as to contribute between 30 to 55% of the total energy of the formula. The fat source preferably has a ratio of n−6 to n−3 fatty acids of about 5:1 to about 15:1; for example about 8:1 to about 10:1.

An additional source of carbohydrate may be added to the nutritional composition. It preferably provides about 40% to about 80% of the energy of the nutritional composition. Any suitable carbohydrate may be used, for example sucrose, lactose, glucose, fructose, corn syrup solids, maltodextrin, or a mixture thereof.

Additional dietary fibre may also be added if desired. If added, it preferably comprises up to about 5% of the energy of the nutritional composition. The dietary fibre may be from any suitable origin, including for example soy, pea, oat, pectin, guar gum, acacia gum, fructooligosaccharides, galactoologosaccharides, or a mixture thereof. Suitable vitamins and minerals may be included in the nutritional composition in an amount to meet the appropriate guidelines.

Examples of minerals, vitamins and other nutrients optionally present in the infant formula include vitamin A, vitamin B1, vitamin B2, vitamin B6, vitamin B 3.2, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

The infant formula may optionally contain other substances which may have a beneficial effect such as fibres, lactoferrin, nucleotides, nucleosides, and the like.

One or more food grade emulsifiers may be included in the nutritional composition if desired; for example diacetyl tartaric acid esters of mono- and di-glycerides, lecithin and mono- or di-glycerides or a mixture thereof. Similarly suitable salts and/or stabilisers may be included. Flavours can be added to the composition.

Administration Period

The duration of the administration may vary. While positive effects are expected with relatively short duration of administration (for example, daily administration during one to two weeks for newborns), longer durations are believed to provide an enhanced effect, or, at least, to maintain the effect in older infants (for example, a duration of three, five, eight or 12 months) or in young children (for example, a duration up to the age of 4 or 6 or even 10 years old). Administration may continue up until the child is about fifteen or even about twenty years old. For administration to animals, the corresponding durations apply.

The expectant mother may start to take the MSWP as soon as she is aware of her pregnancy. However, the administration period may also start before pregnancy starts, for example if the female is trying to become pregnant. Administration may start at any time after the pregnancy starts. It may start relatively late in the pregnancy, preferably at month 3, 4, 5, 6, 7, 8 or 9 of the pregnancy, in the case of human pregnancy, or in corresponding periods for other mammals, or up to two weeks before the expected delivery date.

The period of administration can be continuous (for example, up to and including lactation up to weaning), or discontinuous. Continuous administration is preferred for a more sustained effect. However, it is speculated that a discontinuous pattern (for example, daily administration during one week per month, or during alternate weeks) can induce positive effects on the progeny.

The administration may cover at least part of the gestation period and at least part of the lactation period if the newborn is fed with mother's milk, or the equivalent period, should the newborn not be fed with mother's milk. Preferably, the administration period to the expectant mother covers substantially the full length of the gestation period, although this may be less. Similarly, the administration period for the lactating mother preferably covers substantially the full length of the lactation period, although, again, this period may be less.

Preferably, the administration to the mother is by daily intake (to be taken once or twice a day), or weekly intake (to be taken one or twice a week).

The MSWP may be administered to the infant directly. This is the case particularly if the mother does not breastfeed, or after she discontinues breastfeeding. However, an infant who is being breastfed may also receive the MSWP by direct administration.

Preferably, the administration to the infant is by daily intake. For example, if the MSWP is administered as an infant formula, the administration is with each feed, i.e. about four to about six times daily for infants less than one year old, the number of feeds reducing with age. For infants older than one year, the administration may be less, once or twice a day. For toddlers and young children the administration may be daily or weekly (to be taken one or twice a week).

The administration to the infant, either via breastfeeding, or by direct administration, or both methods, may be continued up until the age of six months or even one year or longer. Thus, the MSWP may be administered during lactation, if lactation takes place, or after partial or full weaning. Administration may continue to the infant through the toddler stage and even, up until the age of twenty years old.

Effect of Administration of the MSWP

In a rat model experiment, detailed in Example 1, the effect of MSWP administration on neuronal maturation in the cerebral cortex, which is associated with higher cognitive function, was evaluated.

In this experiment, rat pups which had experienced maternal diet induced intra-uterine growth retardation (PR group), and pups which had not experienced IUGR (CTRL) were supplemented, from 2 days after birth, with water (controls; namely CTRL-w and PR-w) or modified sweet whey protein (PR-MSW P28).

2 weeks after birth, at sacrifice, the neuronal development in the brain was evaluated by the levels of neuronal markers in the cortex.

The present inventors have found that MSWP and/or MSWP-containing compositions of the present invention promotes the expression of two proteins involved in neuronal and glial cell growth, survival, plasticity and differentiation (notably, Brain Derived Neurotrophic Factor (BDNF)) and in neuronal myelination (notably, MBP).

Increased Expression of Brain Derived Neurotrophic Factor (BDNF)

Brain Derived Neurotrophic Factor (BDNF) is a neurotrophic factor that supports the survival, growth and differentiation of neurons [Huang, E. J. and Reichardt, L. F. (2001)]. It is a potent modulator of synaptic plasticity (Kiriana K. Et al., Brain-Derived Neurotrophic Factor: A Dynamic Gatekeeper of NeuralPlasticity, Current Molecular Pharmacology, 2010, 3, 12-29, Review). In the brain, BDNF is active in the cortex, in areas vital to learning and higher thinking and there are many reports in the literature linking BDNF with learning and memory.

It has been reported that drug induced improvements in learning and memory dysfunction in rats are associated with increased expression levels of BDNF [Dai, M. H., et al. (2011); Effect of venlafaxine on cognitive function and hippocampal brain-derived neurotrophic factor expression in rats with post-stroke depression, *Zhejiang Da XueXueBao Yi Xue Ban,* 40(5): 527-34].

Thus, reduced or de-regulated BDNF expression in the cortex of the infant or foetus may lead to impaired learning and memory as important domains of cognitive functioning in the infant which may continue through childhood and into adulthood.

The levels of BDNF were evaluated in the cortex of pups at sacrifice (PND14). The results are shown in FIG. 1. It was reduced, but not significantly, in PR-w pups as compared to CTRL-w.

The supplementation with the MSW P28 significantly increased the mature BDNF levels as compared to PR-w, while supplementing with the growth factor concentrate had no effect.

Considering these data and the known role of BDNF in neuronal survival, growth and differentiation processes, the increased expression level observed in the current animal model likely translates into biological and cognitive benefits and neuroprotection, during the postnatal development.

Increased Expression of Myelin Basic Protein (MBP)

Figure 2:
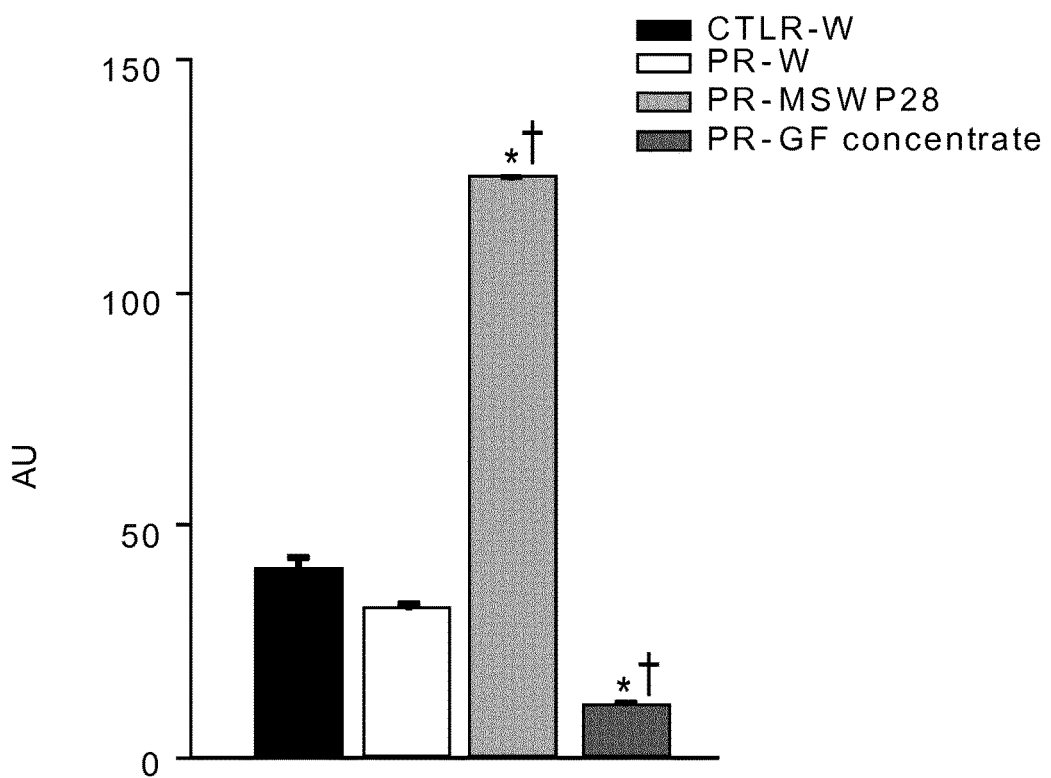
FIG. 2 Myelin Basic protein MBP protein level in the cortex of CTRL-w, PR-W and PR pups supplemented with different milk fractions. Results are expressed in arbitrary units and are medians±SEMedian, n=6, P<0.05; * vs. CTRL-W and † vs. PR-W. Abbreviations are PR: protein restriction; W: water; MSWP28: modified sweet whey P28; GF: Growth factor.

Expression levels of Myelin Basic Protein (MBP) were measured in the animal model of Example 1. The results are shown in FIG. 2.

The level of MBP was evaluated in the cortex of pups at sacrifice (PND14). In PR-W pups, it was maintained at a level similar to that of CTRL-W (FIG. 2). The MSWP28 significantly increased the MBP level in the cortex, while the growth factor concentrate did not induce such an effect. The other milk fractions had either no effect or significantly decreased MBP protein levels.

MBP (Myelin Basic Proteins) are proteins of great importance in the process of myelination of nerves. They are well known as major protein constituents of the myelin membrane, and as such they are among the most abundant proteins in the CNS [Fulton et al. (2010), The multiple roles of myelin protein genes during the development of the oligodendrocyte. ASN NEURO 2(1):art:e00027.doi: 10.1042/AN20090051].

The myelination process is important to convey fast neural signal propagation, allowing effective tissue connectivity within different brain regions, and improving neural pathways connecting separate brain regions required for cognitive, sensory and motor functions.

Myelination plays a key role in the developmental phase of the human brain, continuing for at least 10 to 12, and up to 20 years after birth before being completed. [Baumann, N. and Pham-Dinh, D. (2001)]. The rate of development of myelination, therefore, determines the rate of development of related brain functions.

Considering these data and the known role of MBP in the process of nerve myelination, the increased protein expression level following supplementation with MSWP28 milk fraction likely translates into myelination and cognitive benefits.

Thus, administration of MSWP upregulates MBP expression, therefore ensuring that adequate, or even optimal levels of myelination occur in the young mammal. This ensures effective tissue connectivity within different brain regions, and healthy development of neural pathways connecting separate brain regions required for cognitive, sensory and motor functions.

The administration of MSWP promotes the provision of an excellent foundation for optimal brain growth in both term- and preterm infants, by up-regulating the expression of markers like MBP and BDNF.

As evidenced by the MSWP-induced increased expression levels of two important biomarkers (BDNF and MBP) in Example 1, the administration of MSWP to young mammals promotes the establishment of the processes controlled by these biomarkers; this translates into the healthy establishment of the cerebral cortex and its associated neural pathways necessary for normal cognitive function in the young mammal. Thus, administration of MSWP also prevents or reduces in the severity of cognitive function impairment in a young mammal, in particular in those young mammals at risk of suffering or is suffering from cognitive function impairment.

Thus, administration of MSWP prevents or treats disorders such as impaired learning ability, loss of, or impaired higher reasoning and executive functions, memory impairment, concentration difficulties, delay in language development, abnormally low intelligence, abnormally low mental performance, mood deregulation/disturbance, or autism in children from birth to early adulthood (20 years old).

Neuronal maturation has been positively impacted, in particular, in the structures of the brain associated with cognitive function. Neuronal growth, survival, plasticity and differentiation has been positively impacted by increased expression of BDNF. Signal transmission in the brain has been positively impacted by the increased expression of MBP which supports myelination.

Thus, MSWP may be administered, when there has been already observed a retardation in the development of the CNS and, in particular, in the brain. This may follow, for example, any stress situations, such as those affecting the foetus (in utero) such as IUGR, that may have occurred following any adverse event during the gestation (for example, active or passive smoking of the mother, medication of the mother, low placenta quality, abnormal placenta positioning, malnutrition of the mother and/or the foetus, etc). A retardation in the development of the CNS and, in particular, in the brain may also occur in newborns (hypoxia-ischemia at birth, oxygen therapy and hyperoxia, inflammation, need for parenteral support, etc.), or any cause leading to oxidative stress.

In infants, the MSWP and/or the MSWP containing compositions of the present invention may be used prophylactically to prevent disorders associated with delayed or impaired development of the cerebral cortex and its associated neural pathways, and, in particular, to protect these structures from any stress, e.g., occurring during the neuronal development period, and—consequently—to limit and/or prevent stress-induced neuronal growth retardation and associated cognitive function impairment.

The beneficial effect of MSWP on the healthy development of the mammalian central nervous system with respect to effective establishment of cognitive function is elaborated upon in the paragraphs below.

Example 1

Animal Study (Feeding and Sacrifice)

Animal experiments were conducted under authorization No. 2120 granted by the Office Vétérinaire Cantonal, Etat de Vaud. Two months old female Sprague-Dawley rats were obtained after one week of gestation from Harlan, Barcelona. On the day of their arrival, rat dams were placed in individual cages and randomly assigned either to control (CTRL) or protein restricted (PR) groups. Animals had access to food and water ad libitum and were maintained in a 12 hr light/dark cycle.

Diets of CTRL and PR dams are detailed in Table 1. CTRL dams received a control diet containing 20% protein (casein) in keeping with standard rat protein requirement during gestation [Reeves, P. G., Nielsen, F. H., Fahey, G. C., JR. 1993. AIN-93 Purified Diets for Laboratory Rodents: Final Report of the American Institute of Nutrition Ad Hoc Writing Committee on the Reformulation of the AIN-76A Rodent Diet. J. Nutr. 123:1939-1951]. PR dams received a PR diet containing 10% protein (casein). Both diets were iso-caloric, the protein deficit being balanced by addition of corn starch.

TABLE 1

Composition of control (CTRL) and protein restricted (PR) AIN-93G diets

| Components | Diets | |
|---|---|---|
| | CTRL | PR |
| Cornstarch | 53 | 63 |
| Caseine (K-Caseinate) | 20 | 10 |
| Sucrose | 10 | 10 |
| Soybean oil | 7 | 7 |
| Cellulose | 5 | 5 |
| Mineral mix AIN-93G | 4 | — |
| Mineral mix AIN-93M | — | 4 |
| Vitamin mix AIN-93 | 1 | 1 |
| Choline Bitartrate | 0.25 | 0.25 |
| L-Cysteine | 0.3 | 0.3 |
| Tert-buthylydroquinone | 0.0014 | 0.0014 |

CTRL and PR dams received their respective diets during both gestation and lactation until the day of sacrifice (postnatal day 3.4 (PND 3.4)).

On PND 2, pups were randomly assigned to dams from the same experimental group, and litter size was adjusted to 9 pups per dam with a minimal number of four to five males per litter.

From PND 2 till PND14, a daily hand/pipette feeding supplementation of water or of one of the following milk fractions were administered to control or treated groups, respectively, administered to control or treated groups, respectively. The volume of supplementations was gradually adapted to match the growth of rat pups (150 µl/100 g body-weight). It provided 1-5 mg protein per day per pup.

The groups and diets were as follows:
1) CTRL-w: CTRL pups born from CTRL dams, receiving a supplementation of water.
2) PR-w: PR pups born from PR dams, receiving a supplementation of water.
3) PR-MSWP28: PR pups born from PR dams, receiving a supplementation of MSWP28.
5) PR-GF concentrate: PR pups born from PR dams, receiving a supplementation of GF concentrate.

The milk fractions were:
MSWP28: Sweet whey modified using a Nestlé proprietary process (removal of cGMP). The MSWP fraction contains approximately 28% protein, of which CGMP accounts for, 2 to 3% of total protein.
GF concentrate: Growth factor concentrate commercialized by Tatua, New Zealand. It contains enriched levels of IGFs and TGFs.

They were administered to pups as isonitrogeneous supplementations (12% proteins).

At sacrifice (PND14, n=6/group), pups were sacrificed by decapitation after halothane anaesthesia. The skull was opened, the whole brain was removed, the cortex was rapidly dissected and immediately frozen in liquid nitrogen before storage at −80° C. until further use.

Evaluation of Protein Expression Levels

After isolation, the hippocampus and cortex from PND14 pups of each group were homogenized with a ball beater Tissue Lyser II (Qiagen, USA), in a solution of PBS, pH 7.4, and a complete protease inhibitor cocktail (30 mg tissue per 500 µl solution buffer, Roche Diagnostics, Mannheim, Germany). The protein concentration was determined (BCA, Bio Rad). Proteins (20-40 micrograms, depending on the marker to assess) were separated by SDS-Page, transferred to nitrocellulose membrane and subsequently blocked in 3% BSA. The relative levels of BDNF (Brain-Derived Neurotrophic Factor) and MBP (Myelin Basic Protein) were assessed using the specific antibodies Rb a BDNF (Santa Cruz) and Mse α MBP (Millipore). Detection was made using HRP-chemiluminescence reagents (ECL plus, Amersham), and quantified by using the software AIDA Basic.

Statistics

The effect of protein restriction was evaluated by comparing PR with CTRL groups. The effect of the milk fraction supplementations was evaluated by comparing PR-supplemented group with PR-w. An eventual restoration to CTRL levels was evaluated by comparing each PR-supplemented group with the CTRL-w group. Nonparametric methods were used to analyse the data. Wilcoxon rank sum test was used to test the differences between the treatments. Hodges-Lehmann estimate of the pair-wise treatment difference with its 95% confidence interval was also obtained.

Example 2

An example of the composition of an infant formula for use according to the present invention is given below. This composition is given by way of illustration only. The protein source is a mixture of 60% MSWP28 and 40% casein.

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| *Bifidobacterium lactis* (NCC2818) | $2 \times 10^7$ cfu/g of powder | |

The invention claimed is:

1. A method for promoting a healthy establishment of cognitive function and/or repair of or reduction in a severity of cognitive function impairment in a young mammal, the method comprising administering to the young mammal in need thereof an effective amount of a composition comprising a modified sweet whey protein preparation, wherein the modified sweet whey protein (MSWP) preparation comprises 28 wt % to 99 wt % protein, and
    wherein the MSWP contains 0 to 3% caseino-glyco-macropeptide (CGMP) by weight of the total proteins.

2. The method according to claim 1, wherein the cognitive function impairment is selected from the group consisting of delayed learning ability, impaired learning ability, loss of executive functions, poor development of executive functions, higher reasoning impairment, memory impairment, delay in language development, learning disabilities, abnormally poor concentration, attention deficit hyperactivity disorder (ADHD), abnormally decreased intelligence, abnormally poor mental performance, mood disturbance, autism, and combinations thereof.

3. The method according to claim 1, wherein the young mammal is a non-human.

4. The method according to claim 1, wherein the young mammal is selected from the group consisting of a human fetus, a pre-term infant, a term-born infant, a toddler, a child and a young adult.

5. The method according to claim 1, wherein the young mammal has experienced or is experiencing a condition selected from the group consisting of intrauterine growth retardation (IUGR); hypoxemia-ischemia at birth; is predicted to have or is born with a low, very low, or extremely low birth weight; small for gestational age; cognitive function impairment in utero, during, or after birth; and combinations thereof.

6. The method according to claim 1, wherein the young mammal is a fetus, and administration to the fetus is via the expectant mother.

7. The method according to claim 1, wherein the young mammal is an infant, and administration to the infant is direct or indirect via the lactating mother.

8. The method according to claim 1, wherein the administration period for the young mammal is at least 4 weeks.

9. The method according to claim 1, wherein the young mammal is a child or a young adult, and the administration period for the child is up until the child is up to fifteen years old, and the administration period for the young adult is until early adulthood, approximately 20 years old.

10. The method according to claim 1, wherein the young mammal is an infant or toddler, and the composition is administered directly to the infant or toddler in a form selected from the group consisting of a pure form, diluted in water or breast milk, a food supplement, a milk fortifier, a milk support used during trophic feeding, an infant formula for premature infants, a starter formula, a follow-on formula, a growing-up milk and a milk based drink.

11. The method according to claim 1, wherein administration to the young mammal is orally.

12. The method according to claim 1, wherein the composition is administered to the young mammal at a dose of 1.6-3.2 g protein/100 kcal.

13. The method according to claim 1, wherein the composition comprises at least one prebiotic.

14. The method according to claim 1, wherein the composition comprises at least one probiotic.

15. The method according to claim 1, wherein the modified sweet whey protein preparation comprises 30 wt % to 99 wt % of proteins, of which caseino-glyco-macropeptide (CGMP) is 0%-3% by weight of the total proteins.

16. The method according to claim 1, wherein the modified sweet whey protein preparation comprises approximately 28 wt % of proteins, of which caseino-glyco-macropeptide (CGMP) is 2%-3% by weight of the total proteins.

17. The method according to claim 1, wherein the composition comprises about 9.0 wt % to about 10.0 wt % of MSWP.

18. The method according to claim 17, wherein the composition comprises about 9.5 wt % of MSWP.

* * * * *